United States Patent [19]

Jaeger

[11] 4,067,916
[45] * Jan. 10, 1978

[54] PROCESS FOR THE MANUFACTURE OF PERFLUORALKYL IODIDES

[75] Inventor: Horst Jaeger, Bettingen, Switzerland

[73] Assignee: Ciba-Geigy AG, Basel, Switzerland

[*] Notice: The portion of the term of this patent subsequent to Jan. 19, 1988, has been disclaimed.

[21] Appl. No.: 575,564

[22] Filed: May 8, 1975

Related U.S. Application Data

[63] Continuation of Ser. No. 351,118, April 13, 1973, abandoned, which is a continuation of Ser. No. 2,655, Jan. 13, 1970, abandoned.

[51] Int. Cl.$^2$ .................. C07C 19/07; C07C 19/09
[52] U.S. Cl. .................. 260/653.1 T; 260/658 C
[58] Field of Search .................. 260/653.1 T, 658 C

[56] References Cited

U.S. PATENT DOCUMENTS

| 3,083,238 | 3/1963 | Hauptschein et al. | 260/653.1 T |
|---|---|---|---|
| 3,213,149 | 10/1965 | Takahashi et al. | 260/658 C |
| 3,283,020 | 11/1966 | Parsons | 260/653.1 T |
| 3,404,189 | 10/1968 | Blochl | 260/653.1 T |
| 3,454,657 | 7/1969 | Decker et al. | 260/653.1 T |
| 3,557,224 | 1/1971 | Jaeger | 260/653.1 T |
| 3,631,115 | 12/1971 | Nakagawa et al. | 260/653.1 T |

FOREIGN PATENT DOCUMENTS

| 244,066 | 1/1960 | Australia | 260/658 C |
|---|---|---|---|
| 13,845 | 11/1961 | Israel | 260/658 C |
| 1,127,045 | 9/1968 | United Kingdom | 260/653.1 T |
| 920,855 | 3/1963 | United Kingdom | 260/658 C |

OTHER PUBLICATIONS

Asscher et al., J. Chem. Soc. 1961, 2261–2264.

*Primary Examiner*—C. Davis
*Attorney, Agent, or Firm*—Prabodh I. Almaula; Robert McC. Roberts

[57] ABSTRACT

A process is provided for the manufacture of fluoralkyliodides of high molecular weight from the corresponding perfluoralkyliodides of lower molecular weight. In this process a perfluoralkyliodide is telomerized with a perfluorethylene or a perfluorpropylene each optionally containing at most one chlorine atom, and an amine, in the presence of a metal salt of a metal of groups IIIa, IIIb to VIIIb of the 4th to 6th period or of groups Ia or IIa of the Period Table as a catalyst at 0° to 350° C and under a pressure from 0 to 200 atmospheres (gauge).

The so-obtained products are useful as intermediates for the manufacture of carboxylic acids or alcohols or for reaction with non-fluoro compounds. The products thus obtained may be used as agents for conferring oleophobic or hydrophobic proerties, as soil release agents or also as hydraulic fluids.

10 Claims, No Drawings

PROCESS FOR THE MANUFACTURE OF PERFLUORALKYL IODIDES

This is a continuation of application Ser. No. 351,118, filed on Apr. 13, 1973, which is a continuation of application Ser. No. 2,655 filed on Jan. 13, 1970 and said applications now abandoned.

The subject of the invention is a process for the manufacture of perfluoralkyl iodides of higher molecular weight from the corresponding perfluoralkyl iodides of lower molecular weight, characterised in that a) perfluoralkyl iodides are telomerised with b) perfluorethylene or perfluoropropylene, which optionally contain at most one chlorine atom, and c) an amine, in the presence of d) a metal salt of a metal of groups III a, III b to VIII b of the 4th. to 6th. period or groups I a or II a of the periodic system, as the catalyst, at 0° to 350° C and 0 to 200 atmospheres gauge.

The quantity ratios of the components (a), (b), (c) and (d) vary within rather wide limits depending on how far telomerisation is to be carried out and what properties the end products are to have. The preferred procedure is that 1 mol of component (a) is telomerised with 1 to 10 mols of component (b) and 0.05 to 10 mols of component (c) in the presence of 0.003 to 0.3 mol of component (d).

The perfluoralkyl iodides to be used according to the invention can be both in the form of monoiodides and of diiodides. These perfluoralkyl iodides of component a), also called telogens, are preferably branched or unbranched perfluoralkyl iodides with 1 to 10 carbon atoms, and also cyclic perfluoralkyl iodides with 4 to 6 ring carbon atoms. The following may for example be mentioned as suitable telogens: trifluoromethyl iodide, pentafluorethyl iodide, heptafluoropropyl-1 or heptafluoropropyl-2 iodide, undecafluorocyclohexyl iodide, decafluorocyclohexyl-1,3 diiodide or tetrafluorethyl-1,2 diiodide. Preferably, however, branched or unbranched perfluoralkyl monoiodides or diiodides with 1 to 3 carbon atoms are used.

In the process according to the invention, tetrafluorethylene or hexafluoropropylene are preferably used as component b), also called taxogens. However, olefins such as trifluorethylene, trifluorochlorethylene or pentafluorochloropropylene are also employed for the telomerisation.

Preferably, 0.05 to 1 mol of component (c) is used per 1 mol of component (a), where tetrafluorethylene is employed as component (b).

The amines which can be used as component (c) are especially primary, secondary or tertiary aliphatic, heterocyclic or aromatic amines. Amines which contain at least one oxygen atom in the molecule are preferred. Here amines which contain at least one hydroxyl group in the molecule are particularly suitable. Amines which are capable of forming an amphoteric configuration, such as the alkanolamines, are of particular interest. Such alkanolamines preferably contain at most 6 carbon atoms.

Individually, the following amines may for example be mentioned: N-ethylethanolamine, aminoethylisopropanolamine, diethylethanolamine, N-(2-hydroxyethyl)-ethylenediamine, isopropanolamine, triisopropanolamine, N-ethylethanolamine, N-methylethanolamine; especially diethanolamine, triethanolamine and preferably monoethanolamine. Further possibilities are also amines such as N-hydroxyethylmorpholine, morpholine, N-hydroxyethylpiperazine, 3-diethylaminophenol, glycerine or diethylamine.

The amine (= component c)) can exert a double function in the present process. On the one hand, it exerts a catalytic accelerating effect on the telomerisation together with the metal salt (= component d)), and on the other hand it can also act as a (co-)taxogen, especially if hexafluoropropylene is employed as component b).

The telomerisation products manufactured according to the invention can accordingly contain the telomerised-on residues of the following formulae:

1. $—(R_1)_n - I$,
2. $—(R_1)_n - R_2 - I$,
3. $—(R_1)_n - O - R_2 - I$,
4. $—(R_1)_n - NH - R_2 - I$,
5. $—O - R_2 - I$,
6. $—NH - R_2 - I$, wherein $R_1$ denotes the perfluoralkylene residue of the component (b), $R_2$ the alkylene residue of the component (c) and n an integer having a value of 1 to 10.

Amongst the metal salts to be used according to the invention as component d), metal salts of a metal of groups III *a*, III *b* to VIII *b* of the 4th. to 6th. period or of group I *a* of the periodic system are above all suitable. Amongst these, metal salts of metals of groups III *b* to VIII *b* of the periodic system are in turn preferred. Further, the metal salts of a metal of groups III *b* or VIII *b* of the 4th. or 5th. period, or of a metal of groups IV *b* or V *b* of the 4th. to 6th. period of the periodic system, are of particular interest.

Preferably, yttrium, titanium, zirconium, niobium, tantalum, ruthenium or rhodium salts are therefore used. The halides, such as the bromides, iodides or preferably the chlorides, of the corresponding metals have proved to be particularly advantageous. In addition, corresponding phosphates, carbonates, nitrates, sulphates, cyanides, hydrides, acetylacetonates or ethylates can however also be used.

Suitable representatives of metals of group I *a* are for example sodium and potassium and group II*a* are for example magnesium, calcium, strontium or barium. The metals of group III *a* include gallium, thallium and indium.

All references to the periodic system are references to the periodic system according to Mendelejeff.

The telomerisation according to the invention thus takes place at temperatures of 0 to 350° C, especially 50 to 300° C, and preferably at 100° to 250° C.

Depending on whether the boiling points of the components a), b) and c) are below or above 60° C, the telomerisation is appropriately carried out in an autoclave or in a pressure-free apparatus. In the autoclave, a pressure becomes established which depends on the initially introduced amount of the telogen and of the taxogen. The pressures are 0 to 200 atmospheres gauge, preferably 10 to 100 atmospheres gauge, depending on the reacting components.

The telomerisation takes place trouble-free and in good yields. In all cases product mixtures of perfluoralkyl iodides are obtained, showing a varying degree of telomerisation, as can easily be demonstrated by mass spectrography. The main constituents of the reaction products are as a rule perfluoralkyl iodides which have 4 to 5 mols of component b) telomerised-on per iodine residue per mol of component a). Products which have 3 or even only 2 mols of component b) added on per iodine residue are also produced in small amounts, and so-called 1:1 adducts are also produced in very small amounts. Further, products can also arise which contain a residue of one of formulae (2) to (6) per iodine residue per mol of component a).

In the telomerisation, according to the invention, of perfluoralkyl iodides with hexafluoropropylene, telomers of perfluoralkyl iodide and tetrafluorethylene can also be produced in addition to the expected telomers of perfluoralkyl iodide and hexafluoropropylene. The occurrence in the end products of structural elements derived from tetrafluoroethylene can be explained by assuming that the hexafluoropropylene decomposes to form intermediate perfluoromethylene radicals, and that these radicals are then re-combined to give tetrafluorethylene (compare J. org. Chem. 27, 3425 (1962)). The catalysts used according to the invention favour the formation of so-called carbenes.

In addition to the fact that the telomerisation with the catalyst system used according to the invention takes place so free of troubles and effectively, the system metal saltamine used according to the invention has the further advantage over the previously used catalyst system such as $IF_5$-$SbF_3$, $IF_5$-$AlCl_3$ or HF-$SF_4$ that it is non-corrosive and that the apparatuses used, and simultaneously therewith the requisite precautionary measures, are significantly simplified.

The perfluoralkyl iodides manufactured according to the invention can be used as intermediate products for the manufacture of carboxylic acids or alcohols by saponification. They can also be used for telomerisation or for reaction with compounds which do not contain fluorine. The products thus obtained above all serve as agents for conferring oleophobic or hydrophobic properties, or as soil release agents or hydraulic fluids.

Percentages in the examples which follow are percentages by weight.

EXAMPLE 1

100 mg of zirconium tetrachloride and 5 g of ethanolamine are weighed into a 300 ml stainless steel autoclave. The autoclave is closed, cooled to −70° C, flushed with nitrogen and evacuated.

30 g of n-perfluoropropyl iodide (0.1 mol) and 58 g of tetrafluorethylene (0.58 mol) are then injected. A slow reaction starts at 130° C and 30 atmospheres gauge. The reaction is kept for 72 hours at 100° to 105° C. In the course thereof the pressure drops to 8 atmospheres gauge. On releasing the pressure, 20 g of n-perfluoropropyl iodide are recovered.

A brown waxy product is isolated from the autoclave, which after washing with water weighs 12.5 g. 9.2 g of sublimate of melting point 150° to 155° C can be obtained therefrom.

$CF_3CF_2CF_2(CF_2CF_2)_nI$ is found by mass spectroscopy and gas chromatography.

| n | Molecular weight | Content |
|---|---|---|
| 8 | 1096 | 0.64% |
| 7 | 996 | 6.43% |
| 6 | 896 | 19.30% |
| 5 | 796 | 34.50% |
| 4 | 696 | 39.18% |

Relative to an average molecular weight of 796 ($n=5$), the yield is 34.2% of theory (26.9 g).

The Yield is calculated as follows:

| Amount of n-perfluoropropyl iodide employed | 30 g |
|---|---|
| Amount of perfluoropropyl iodide recovered | 20 g |
| Amount of n-perfluoropropyl iodide consumed | 10 g |

10 g = 0.0338 mol
At a molecular weight of 796, n = 5.
5 × 0.0338 = 0.169 mol = 16.9 g of consumed tetrafluorethylene Theoretical yield: 10. g
16.9 g
26.9 g → $\frac{9.2 \times 100}{26.9}$ = 34.2%

EXAMPLE 2

50 g of perfluorisopropyl iodide, 106 g of hexafluoropropylene, 200 mg of $ZrCl_4$ and 5 g of ethanolamine are heated to 160° C in a 300 ml autoclave. The autogenic pressure of the reaction is 37 atmospheres gauge. Over the course of 8 hours, the pressure drops to 33 atmospheres gauge and remains constant.

The autoclave is cooled to room temperature and on releasing the pressure 72 g of hexafluoropropylene and 22.7 g of perfluorisopropyl iodide are recovered.

3.2 g of perfluoralkyl iodide of molecular weight (M) 396, 496, 446, and 8.5 g of sublimate (subliming at 150° to 155° C/5 mm Hg) are obtained from the residue.

The perfluoralkyl iodides correspond to the formulae:

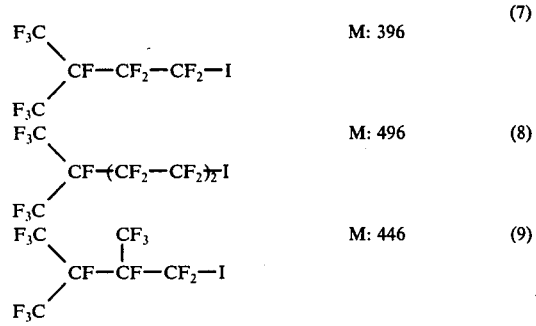

The sublimate is a mixture of compounds which have been produced by telomerisation of perfluorisopropyl iodide with hexafluoropropylene and ethanolamine, and which correspond to the following probable formulae:

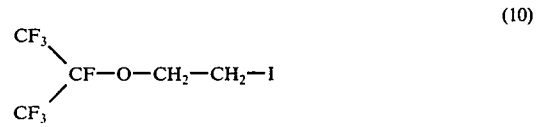

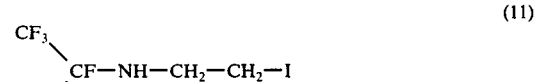

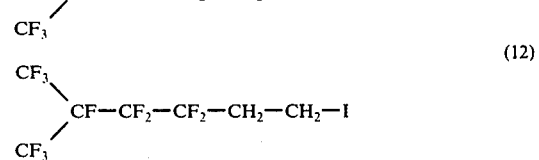

EXAMPLE 3

50 g of perfluorisopropyl iodide, 107 g of hexafluoropropylene, 5 g of ethanolamine and 200 mg of yttrium trichloride are heated in an autoclave to 110° C for 48 hours. In the course thereof, the autogenic pressure of the reaction falls from an original 25 atmospheres gauge to 12 atmospheres gauge.

The autoclave is cooled to room temperature and 18 g of hexafluoropropylene and 5 g of perfluorisopropyl iodide are recovered.

9.1 g of sublimate are obtained from the residue. The sublimate is a mixture of compounds which have been produced by telomerisation of perfluorisopropyl iodide with hexafluoropropylene and ethanolamine. These compounds probably correspond to the following formulae:

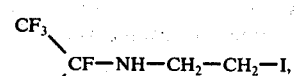 (13)

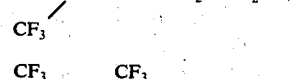 (14)

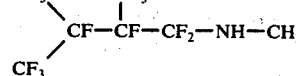 (15)

with the compound of formula (14) representing the main component.

EXAMPLE 4

47 g of perfluorethyl iodide (0.191 mol), 52 g of trifluorochlorethylene (0.52 mol), 100 mg of titanium tetrachloride and 5 of ethanolamine are reacted according to the process of example 1.

The reaction starts at 152° C and 38 atmospheres gauge. The autoclave is kept at 150° C for 64 hours. In the course thereof the pressure drops to 35 atmospheres gauge. On releasing the pressure, 30 g of perfluorethyl iodide are recovered. 42 g of a brown solid product are isolated from the autoclave.

Sublimation at 2 mm Hg and 40° C yields 8.4 g of a liquid yellow telomer. The remainder of the substance decomposes during the sublimation, with iodine being isolted. Mass spectroscopy shows:

| n | Molecular weight |
|---|---|
| 1 | 362 |
| 2 | 478 |
| 3 | 594 |

The yield is 25.3% of theory calculated relative to an average molecular weight of 478.

EXAMPLE 5

63 g of perfluoroethyl iodide (0.256 mol), 52 g of tetrafluoroethylene (0.52 mol), 200 mg of zirconium tetrachloride and 5 g of ethanolamine are reacted according to the process of example 1.

The reaction starts at 140° C and 46 atmospheres gauge. The autoclave is kept at 140° C for 24 hours. In the course thereof, the pressure drops to 26 atmospheres gauge. On releasing the pressure, 20 g of perfluorethyl iodide are recovered. 35 g of a brown product are isolated from the autoclave.

Sublimation at 1 mm Hg yields 29.8 g of a white telomer of melting point 199 to 205° C. Mass spectroscopy and gas chromatography show:

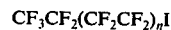

| n | Molecular weight | Content, % |
|---|---|---|
| 9 | 1146 | 6.5 |
| 8 | 1046 | 1.01 |
| 7 | 946 | 8.28 |
| 6 | 846 | 20.78 |
| 5 | 746 | 41.55 |
| 4 | 646 | 15.77 |
| 3 | 546 | 2.81 |
| 2 | 446 | 8.11 |
| 1 | 346 | 1.18 |

The yield, calculated relative to an average molecular weight of 746, is 39.8% of theory.

EXAMPLE 6

60 g of perfluoroethyl iodide (0.244 mol), 60 g of tetrafluoroethylene (0.6 mol), 200 mg of yttrium trichloride and 5 g of ethanolamine are reacted according to the process of example 1.

The reaction starts at 140° C and 51 atmospheres gauge. The autoclave is kept at 140° C for 21 hours. In the course thereof, the pressure drops to 30 atmospheres gauge. On releasing the pressure, 35 g of perfluoroethyl iodide are recovered. 46 g of a yellow product are isolated from the autoclave.

Sublimation yields 22.76 g of an ivory-coloured telomer of melting range 144° to 198° C.

Mass spectroscopy and gas chromatography show:

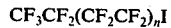

| n | Molecular weight | Content, % |
|---|---|---|
| 16 | 1846 | 0.6 |
| 15 | 1746 | 0.6 |
| 14 | 1646 | 1.2 |
| 13 | 1546 | 6.0 |
| 12 | 1446 | 6.0 |
| 11 | 1346 | 6.05 |
| 10 | 1246 | 0.36 |
| 9 | 1146 | 1.30 |
| 8 | 1046 | 3.60 |
| 7 | 946 | 5.67 |
| 6 | 846 | 13.32 |
| 5 | 746 | 22.67 |
| 4 | 646 | 13.72 |
| 3 | 546 | 1.30 |
| 2 | 446 | 4.90 |
| 1 | 346 | 12.65 |

The yield, calculated relative to an average molecular weight of 746, is 30.3% of theory.

EXAMPLE 7

72 g of perfluorethyl iodide (0.292 mol), 56 g of tetrafluorethylene (0.56 mol), 200 mg of rhodium trichloride and 5 g of ethanolamine are reacted according to the process of example 1.

The reaction starts at 100° C and 35 atmospheres gauge. The temperature rapidly rises to 160° C and the pressure to 50 atmospheres gauge. The autoclave is kept at 150° C for 24 hours. In the course thereof the pressure drops to 30 atmospheres gauge. On releasing the pressure, 20 g of perfluorethyl iodide are recovered. 58 g of a brown waxy product are isolated from the autoclave. Sublimation yields 39.1 g of a yellowish telomer of melting point 199° to 205° C.

Mass spectroscopy of gas chromatography show:

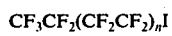

| n  | Molecular weight | Content, % |
|----|------------------|------------|
| 13 | 1546             | 1.10       |
| 12 | 1446             | 2.20       |
| 11 | 1346             | 5.68       |
| 10 | 1246             | 6.94       |
| 9  | 1146             | 10.41      |
| 8  | 1046             | 3.47       |
| 7  | 946              | 7.10       |
| 6  | 846              | 10.76      |
| 5  | 746              | 15.00      |
| 4  | 646              | 19.54      |
| 3  | 546              | 9.58       |
| 2  | 446              | 1.86       |
| 1  | 346              | 6.37       |

The yield, calculated relative to an average molecular weight of 746, is 47.55% of theory.

EXAMPLE 8

58 g of perfluoroethyl iodide (0.236 mol), 55 g of tetrafluoroethylene (0.55 mol), 200 mg of tantalum pentachloride and 55 g of ethanolamine are reacted according to the process of example 1.

The reaction starts at 150° C and 38 atmospheres gauge. The autoclave is kept at 150° C for 24 hours. In the course thereof, the pressure drops to 21 atmospheres gauge. On releasing the pressure, 15 g of perfluorethyl iodide are recovered. 35 g of a smeary brown product are isolated from the autoclave.

Sublimation yields 20.2 g of a white telomer with a melting range of 196° to 230° C.

Mass spectroscopy and gas chromatography show:

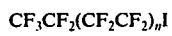

| n  | Molecular weight | Content, % |
|----|------------------|------------|
| 13 | 1546             | 0.63       |
| 12 | 1446             | 1.69       |
| 11 | 1346             | 5.63       |
| 10 | 1246             | 6.54       |
| 9  | 1146             | 8.86       |
| 8  | 1046             | 15.26      |
| 7  | 946              | 13.15      |
| 6  | 846              | 8.37       |
| 5  | 746              | 15.33      |
| 4  | 646              | 16.38      |
| 3  | 546              | 8.16       |

Calculated relative to an average molecular weight of 746, the yield is 26.9% of theory.

EXAMPLE 9

40 g of perfluorethyl iodide (0.162 mol), 55 g of tetrafluorethylene (0.55 mol), 200 mg of ruthenium trichloride and 5 g of ethanolamine are reacted according to the process of example 1.

The reaction starts at 135° C and 45 atmospheres gauge. The temperature rapidly rises to 150° C and the pressure to 42 atmospheres gauge. The autoclave is kept at 150° C for 24 hours. In the course thereof, the pressure drops to 38 atmospheres gauge. On releasing the pressure, 20 g of perfluorethyl iodide are recovered. 17 g of a beige-coloured product are isolated from the autoclave.

Sublimation yields 4 g of a beige telomer with a melting range of 147° to 184° C. The remainder can no longer be sublimed.

Mass spectroscopy and gas chromatography show:

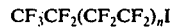

| n       | Molecular weight | Content, %      |
|---------|------------------|-----------------|
| 16 to 4 | 1846 to 746      | uniform scatter |

EXAMPLE 10

40 g of perfluorethyl iodide (0.162 mol), 38 g of tetrafluorethylene (0.38 mol), 200 mg of chromium trichloride and 5 g of ethanolamine are reacted according to the process of example 1.

The reaction starts at 110° C and 46 atmospheres gauge. The autoclave is kept at 110° C for 22 hours. In the course thereof, the pressure drops to 38 atmospheres gauge. On releasing the pressure, 30 g of perfluorethyl iodide are recovered. 15 g of a brown smeary product are isolated from the autoclave.

Sublimation yields 3.88 g of a white smeary telomer with a melting range of 195° to 220° C.

Mass spectroscopy and gas chromatography show:

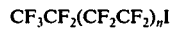

| n | Molecular weight | Content, % |
|---|------------------|------------|
| 7 | 946              | 2.07       |
| 6 | 846              | 5.93       |
| 5 | 746              | 22.16      |
| 4 | 646              | 69.84      |

Calculated relative to an average molecular weight of 746, the yield is 12.9% of theory.

EXAMPLE 11

55 g of perfluorethyl iodide (0.224 mol), 40 g of tetrafluorethylene (0.40 mol), 200 mg of yttrium trichloride and 5 g of ethanolamine are reacted according to the process of example 1.

The reaction starts at 140° C and 41 atmospheres gauge. The autoclave is kept at 140° C for 18 hours. In the course thereof, the pressure drops to 30 atmospheres gauge. On releasing the pressure, 25 g of perfluoroethyl iodide are recovered. 20 g of a solid product are isolated from the autoclave.

Sublimation yields 8 g of a light yellow telomer with a melting range of 198° to 220° C.

Mass spectroscopy and gas chromatography show:

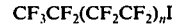

| n | Molecular weight | Content, % |
|---|------------------|------------|
| 8 | 1046             | 6.63       |
| 7 | 946              | 8.72       |
| 6 | 846              | 10.50      |
| 5 | 746              | 20.68      |
| 4 | 646              | 45.88      |
| 3 | 546              | 7.59       |

Calculated relative to an average molecular weight of 746, the yield is 53.4% of theory.

EXAMPLE 12

50 g of perfluorisopropyl iodide (0.169 mol), 50 g of tetrafluorethylene (0.50 mol), 1 g of zirconium tetrachloride and 5 g of ethanolamine are reacted according to the process of example 1.

The reaction starts at 130° C and 40 atmospheres gauge. The autoclave is kept at 130° C for 56 hours. In the course thereof, the pressure drops to 30 atmosphere gauge. On releasing the pressure, 42 g of perfluorisopropyl iodide are recovered. 50 g of a dark brown viscous product are isolated from the autoclave.

Sublimation yields 11.9 g of a solid telomer of melting point 140° to 150° C and 2 g of liquid in the cooling trap.

Mass spectroscopy and gas chromatography show: (from 11.9 + 2.0 g)

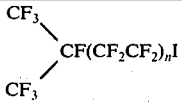

| n | Molecular weight | Content, % |
|---|---|---|
| 7 | 996 | 9.97 |
| 6 | 896 | 14.82 |
| 5 | 796 | 36.08 |
| 4 | 696 | 34.10 |
| 3 | 596 | 3.09 |
| 2 | 496 | 1.87 |
| 1 | 396 | 1.10 |

Calculated relative to an average molecular weight of 796, a yield of 67.8% of theory is obtained.

EXAMPLE 13

50 g of perfluorisopropyl iodide (0.169 mol), 52 g of tetrafluorethylene (0.52 mol), 1 g of titanium tetrachloride and 5 g of ethanolamine are reacted according to the process of example 1.

The reaction starts at 140° C and 49 atmospheres gauge. The autoclave is kept at 140° C for 24 hours. In the course thereof the pressure drops to 23 atmospheres gauge. On releasing the pressure, 32 g of perfluorisopropyl iodide are recovered. 50.0 g of a waxy product are isolated from the autoclave.

Sublimation yields 27.7 g of a telomer of melting point 136° to 148° C, containing liquid and solid constituents.

Mass spectroscopy and gas chromatography show:

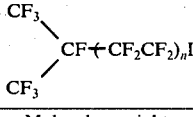

| n | Molecular weight | Content, % |
|---|---|---|
| 9 | 1196 | traces |
| 8 | 1096 | 0.30 |
| 7 | 996 | 1.57 |
| 6 | 896 | 10.00 |
| 5 | 796 | 28.26 |
| 4 | 696 | 28.57 |
| 3 | 596 | 7.68 |
| 2 | 496 | 11.87 |
| 1 | 396 | 11.78 |

Calculated relative to an average molecular weight of 796, the yield is 63.2% of theory.

EXAMPLE 14

212 g of perfluorethyl iodide (0.862 mol), 10 g of tetrafluorethylene (0.10 mol), 1 g of zirconium tetrachloride and 5 g of ethanolamine are reacted according to the process of example 1.

The reaction starts at 128° C and 25 atmospheres gauge. The autoclave is kept at 140° C for 18 hours. In the course thereof the pressure drops from 34 to 30 atmospheres gauge. On releasing the pressure, 188 g of perfluorethyl iodide are recovered. 22 g of a liquid violet product are isolated from the autoclave.

Distillation yields 19.0 g of a violet distillate:
Fraction 1 1.1 g 22 to 35° C
Fraction 2 3.0 g 65° C
Cooling trap 5.15 g Mass spectroscopy and gas chromatography of the above fractions shows:

$CF_3CF_2(CF_2CF_2)_nI$

| n | Molecular weight | Content, % |
|---|---|---|
| 0 | 246 | 73.40 |
| 1 | 346 | 23.21 |
| 2 | 446 | 3.01 |
| 3 | 546 | 0.38 |
| 4 | 646 | traces |

EXAMPLE 15

49 g of perfluorethyl iodide (0.199 mol), 55 g of tetrafluorethylene (0.55 mol), 200 mg of gallium tribromide and 5 g of ethanolamine are reacted according to the process of example 1.

The reaction starts at 150° C and 46 atmospheres gauge. The autoclave is kept at 150° C for 24 hours. In the course thereof, the pressure drops to 26 atmospheres gauge. On releasing the pressure, 15 g of perfluorethyl iodide are recovered. 49 g of a white product are isolated from the autoclave.

Sublimation yields 28.47 g of a white telomer of melting point 87 to 100° C.

Mass spectroscopy and gas chromatography show:

$CF_3CF_2(CF_2CF_2)_nI$

| n | Molecular weight | Content, % |
|---|---|---|
| 10 to 14 | 1246 to 1546 | 1.94 |
| 9 | 1146 | 1.34 |
| 8 | 1046 | 42.13 |
| 7 | 946 | 18.28 |
| 6 | 846 | 6.20 |
| 5 | 746 | 11.20 |
| 4 | 646 | 13.62 |
| 3 | 546 | 5.26 |
| 2 | 446 | 0.13 |

Relative to an average molecular weight of 746, the yield is 38.0% of theory.

EXAMPLE 16

49 g of perfluorisopropyl iodide (0.165 mol), 50 g of tetrafluorethylene (0.50 mol), 1000 mg of thallium-I iodide and 5 g of ethanolamine are reacted according to the process of example 1.

The reaction starts at 130° C and 42 atmospheres gauge. The autoclave is kept at 130° C for 16 hours. In the course thereof, the pressure drops to 31 atmospheres gauge. On releasing the pressure, 43 g of perfluorisopropyl iodide are recovered. 37 g of a brown smeary product are isolated from the autoclave.

Sublimation yields 13.41 g of an ivory-coloured telomer of melting point 125° to 130° C.

Mass spectroscopy and gas chromatography show:

| n | Molecular weight | Content, % |
|---|---|---|
| 9 | 1196 | 2.98 |
| 8 | 1096 | 4.55 |
| 7 | 996 | 8.28 |
| 6 | 896 | 17.97 |
| 5 | 796 | 27.29 |
| 4 | 696 | 30.87 |
| 3 | 596 | 2.09 |
| 2 | 496 | 1.94 |
| 1 | 396 | 4.03 |

The yield, relative to an average molecular weight of 796, is 81.3% of theory.

EXAMPLE 17

50 g of perfluorethyl iodide (0.203 mol), 50 g of tetrafluorethylene (0.50 mol), 200 mg of sodium chloride and 5 g of ethanolamine are reacted according to the process of example 1.

The reaction starts at 130° C and 51 atmospheres gauge. The autoclave is kept at 130° C for 96 hours. In the course thereof, the pressure drops to 47 atmospheres gauge. On releasing the pressure, 20 g of perfluorethyl iodide are recovered. 21.8 g of a drak brown solid product are isolated from the autoclave.

Sublimation yields 6.54 g of a white telomer with a melting range of 205° to 240° C.

Mass spectroscopy and gas chromatography show:

$CF_3CF_2(CF_2CF_2)_nI$

| n | Molecular weight | Content, % |
|---|---|---|
| 9 | 1146 | 0.8 |
| 8 | 1046 | 8.72 |
| 7 | 946 | 27.06 |
| 6 | 846 | 34.40 |
| 5 | 746 | 18.80 |
| 4 | 646 | 10.24 |

Relative to an average molecular weight of 746, the yield is 8.75% of theory (theory = 74.6 g).

EXAMPLE 18

50 g of perfluorisopropyl iodide (0.169 mol), 53 g of tetrafluorethylene (0.53 mol), 1000 mg of potassium iodide and 5 g of ethanolamine are reacted according to the process of example 1.

The reaction starts at 130° C and 39 atmospheres gauge. The autoclave is kept at 140° C for 48 hours. In the course thereof, the pressure drops to 25 atmospheres gauge. On releasing the pressure, 44 g of perfluorisopropyl iodide are recovered. 31.9 g of a borwn smeary product are isolated from the autoclave.

Sublimation yields 13.3 g of a solid telomer with a melting range of 152° to 170° C.

Mass spectroscopy and gas chromatography show:

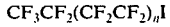

| n | Molecular weight | Content, % |
|---|---|---|
| 8 | 1096 | 0.06 |

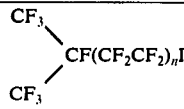

| n | Molecular weight | Content, % |
|---|---|---|
| 7 | 996 | 1.71 |
| 6 | 896 | 10.22 |
| 5 | 796 | 45.94 |
| 4 | 696 | 37.25 |
| 3 | 596 | 4.82 |

The yield, relative to an average molecular weight of 796, is 70.14% of theory.

A redistillation of 44 g of perfluorisopropyl iodide yields: 94.70% M 296, 3.96% M 396, 1.47% M 496 and 0.35% M 596.

EXAMPLE 19

45 g of perfluoroethyl iodide (0.183 mol), 32 g of tetrafluoroethylene (0.32 mol), 1 g of indium acetylacetonate and 5 g of ethanolamine are reacted according to the process of example 1.

The reaction starts at 140° C and 41 atmospheres gauge. The autoclave is kept at 140° C for 72 hours. In the course thereof, the pressure drops to 38 atmospheres gauge. On releasing the pressure, 62 g of a mixture of perfluoroethyl iodide and tetrafluoroethylene are recovered. 13 g of a solid brown product are isolated from the autoclave.

Sublimation yields 3.2 g of a beige telomer with a melting range of 55° to 82° C.

Mass spectroscopy and gas chromatography shows:

$CF_3CF_2(CF_2CF_2)_nI$

| n | Molecular weight | Content, % |
|---|---|---|
| 7 | 946 | 7.62 |
| 6 | 846 | 14.28 |
| 5 | 746 | 60.95 |
| 4 | 746 | 17.15 |

Relative to an average molecular weight of 746, the yield is 21.35% of theory.

EXAMPLE 20

50 g of perfluoroethyl iodide (0.203 mol), 40 g of tetrafluoroethylene (0.40 mol), 200 mg of zirconium tetrachloride and 5 g of diethanolamine are reacted according to the process of example 1.

The reaction starts at 140° C and 38 atmospheres gauge. The autoclave is kept at 140° C for 24 hours. In the course thereof, the pressure drops to 34 atmospheres gauge. On releasing the pressure, 44 g of perfluoroethyl iodide are recovered. 7 g of a dark brown product are isolated from the autoclave.

Sublimation yields 1.9 g of a beige telomer with a melting point of 145° to 150° C.

Mass spectroscopy and gas chromatography shows:

$CF_3CF_2(CF_2CF_2)_nI$

| n | Molecular weight | Content, % |
|---|---|---|
| 1 | 346 | 25 |
| 4 | 646 | 25 |
| 5 | 746 | 35 |

-continued

| n | Molecular weight | Content, % |
|---|---|---|
| 6 | 846 | 10 |
| 3* | $CF_3CF_2(CF_2CF_2)_3CH_2CH_2I$ 547 | 2.5 |
| 4* | $CF_3CF_2(CF_2CF_2)_4CH_2CH_2I$ 674 | 2.5 |

*These by-products correspond to a compound of formula (2) on page 4.

The yield, relative to an average molecular weight of 746, is 10.61% of theory.

EXAMPLE 21

82 g of perfluoroethyl iodide (0.333 mol), 40 g of tetrafluoroethylene (0.40 mol), 200 mg of zirconium tetrachloride and 5 g of triethanolamine are reacted according to the process of example 1.

The reaction starts at 120° C and 39 atmospheres gauge. The autoclave is kept at 120° C for 60 hours. In the course thereof, the pressure drops to 30 atmospheres gauge. On releasing the pressure, 78 g of perfluoroethyl iodide are recovered. 8 g of a solid brown product are isolated from the autoclave.

Sublimation yields 4 g of a white telomer with a melting point of 89 to 98° C.

Mass spectroscopy and gas chromatography show:

$CF_3CF_2(CF_2CF_2)_nI$

| n | Molecular weight | Content, % |
|---|---|---|
| 3 | 546 | 4.75 |
| 4 | 646 | 37.76 |
| 5 | 746 | 29.45 |
| 6 | 846 | 23.14 |
| 7 | 946 | 4.90 |

The yield, relative to an average molecular weight of 746, is 33.10% of theory.

EXAMPLE 22

51 g of perfluoroethyl iodide (0.207 mol), 41 g of tetrafluoroethylene (0.41 mol), 200 mg of zirconium tetrachloride and 5 g of N-ethyl-ethanolamine are reacted according to the process of example 1.

The reaction starts at 140° C and 38 atmospheres gauge. The autoclave is kept at 140° C for 30 hours. In the course thereof, the pressure drops to 32 atmospheres gauge. On releasing the pressure, 48 g of perfluoroethyl iodide are recovered. 4.2 g of a brown solid product are isolated from the autoclave.

Sublimation yields 1.9 g of a yellow telomer with a melting range of 172° to 215° C.

Mass spectroscopy and gas chromatography show:

$CF_3CF_2(CF_2CF_2)_nI$

| n | Molecular weight | Content, % |
|---|---|---|
| 5 | 746 | 42.80 |
| 6 | 846 | 35.75 |
| 7 | 946 | 14.30 |
| 8 | 1046 | 7.15 |

The yield, relative to an average molecular weight of 746, is 20.87% of theory.

EXAMPLE 23

33.5 g of perfluoroethyl iodide (0.136 mol), 29.5 g of tetrafluoroethylene (0.29 mol), 200 mg of zirconium tetrachloride and 5 g of N-(2-hydroxyethyl)-ethylenediamine are reacted according to the process of example 1.

The reaction starts at 140° C and 40 atmospheres gauge. The autoclave is kept at 140° C for 60 hours. In the course thereof, the pressure drops to 28 atmospheres gauge. On releasing the pressure, 20 g of perfluoroethyl iodide are recovered. 12 g of a black solid product are isolated from the autoclave.

Sublimation yields, 3.8 g of a cream-coloured telomer with a melting point of 89° to 98° C.

Mass spectroscopy and gas chromatography show:

$CF_3CF_2(CF_2CF_2)_nI$

| n | Molecular weight | Content, % |
|---|---|---|
| 3 | 546 | 20 |
| 4 | 646 | 20 |
| 5 | 746 | 20 |
| 6 | 846 | 20 |
| 7 | 946 | 20 |

The yield, relative to an average molecular weight of 746, is 6.85% of theory.

EXAMPLE 24

51 g of perfluorethyl iodide (0.207 mol), 51 g of tetrafluoroethylene (0.51 mol), 200 mg of barium iodide and 5 g of ethanolamine are reacted according to the process of example 1.

The reaction starts at 130° C and 43 atmospheres gauge. The autoclave is kept at 130° C for 48 hours. In the course thereof, the pressure drops to 38 atmospheres gauge. On releasing the pressure, 50 g of perfluorethyl iodide are recovered. 6 g of a brown smeary product are isolated from the autoclave.

Sublimation yields 0.85 g of a white telomer with a melting range of 120° to 160° C.

Mass spectroscopy and gas chromatography show:

$CF_3CF_2(CF_2CF_2)_nI$

| n | Molecular weight | Content, % |
|---|---|---|
| 5 | 746 | 56.06 |
| 6 | 846 | 28.79 |
| 7 | 946 | 9.10 |
| 8 | 1046 | 5.30 |
| 9 | 1146 | 0.75 |

The yield, relative to an average molecular weight of 746, is 28.14% of theory.

EXAMPLE 25

50 g of perfluoroethyl iodide (0.203 mol), 48 g of tetrafluoroethylene (0.48 mol), 200 mg of strontium bromide and 5 g of ethanolamine are reacted according to the process of example 1.

The reaction starts at 140° C and 43 atmospheres gauge. The autoclave is kept at 140° C for 60 hours. In the course thereof, the pressure drops to 40 atmospheres gauge. On releasing the pressure, 44 g of perfluoroethyl iodide are recovered. 5 g of a solid brown product are isolated from the autoclave.

Sublimation yields, 2.1 g of a cream-coloured telomer with a melting point of 140° to 150° C.

Mass spectroscopy and gas chromatography show:

$CF_3CF_2(CF_2CF_2)_nI$

| n | Molecular weight | Content, % |
|---|---|---|
| 4 | 646 | 30.63 |
| 5 | 746 | 39.64 |
| 6 | 846 | 18.02 |
| 7 | 946 | 7.21 |
| 8 | 1046 | 1.80 |
| 9 | 1146 | 1.80 |
| 10 | 1246 | 0.90 |

The yield, relative to an average molecular weight of 746, is 11.5% of theory.

EXAMPLE 26

50 g of perfluoroheptyl iodide (0.1008 mol), 35 g of tetrafluoroethylene (0.35 mol), 200 mg of zirconium tetrachloride and 5 g of ethanolamine are reacted according to the process of example 1.

The reaction starts at 120° C and 28 atmospheres gauge. The autoclave is kept at 120° C for 18 hours and then kept at 150° C for 18 hours. In the course thereof, the pressure drops to 25 atmospheres gauge. On stripping by distillation, 39.5 g of perfluoroheptyl iodide are recovered. 14 g of a light yellow smeary product are isolated from the autoclave.

Sublimation yields 12.3 g of a liquid/solid telomer.

| | | |
|---|---|---|
| Fraction 1 boiling point 40° C/15 mm Hg | Distillate 3.7 g | |
| Fraction 2 boiling point 80° C/20 mm Hg | 2.1 g | 12.3 g |
| Fraction 3 boiling point 120° C/20 mm Hg | Sublimate 4.4 g | |
| Fraction 4 boiling point 180° C/20 mm Hg | 2.1 g | |

Mass spectroscopy and gas chromatography show:

$CF_3(CF_2)_6(CF_2CF_2)_nI$

| n | Molecular weight | Content, % |
|---|---|---|
| 1 | 596 | 49.35 |
| 2 | 696 | 38.03 |
| 3 | 796 | 9.49 |
| 4 | 896 | 2.82 |
| 5 | 996 | 0.31 |

The yield, relative to an average molecular weight of 696, is 83.67% of theory.

EXAMPLE 27

50 g of perfluoromethyl iodide (0.255 mol), 52 g of tetrafluoroethylene (0.52 mol), 200 mg of zirconium tetrachloride and 5 g of ethanolamine are reacted according to the process of example 1.

The reaction starts at 130° C and 48 atmospheres gauge. The autoclave is kept at 130° C for 35 hours. In the course thereof, the pressure drops to 42 atmospheres gauge. On releasing the pressure, 98 g of tetrafluoroethylene/perfluoromethyl iodide mixture are recovered. 6 g of dark brown viscous product are isolated from the autoclave.

Sublimation yields 0.7 g of a yellow telomer with a melting point of 90° to 95° C.

Mass spectroscopy and gas chromatography show:

$CF_3(CF_2CF_2)_nI$

| n | Molecular weight | Content, % |
|---|---|---|
| 5 | 696 | 43.48 |
| 6 | 796 | 30.43 |
| 7 | 896 | 17.39 |
| 8 | 996 | 8.70 |

Yield by weight, 17.5% of theory.

EXAMPLE 28

50 g of perfluoroethyl iodide (0.203 mol), 51 g of tetrafluorethylene (0.51 mol), 200 mg of zirconium tetrachloride and 5 g of N-hydroxyethylmorpholine are reacted according to the process of example 1.

The reaction starts at 150° C and 43 atmospheres gauge. The autoclave is kept at 150° C for 30 hours. In the course thereof the pressure drops to 37 atmospheres gauge. On releasing the pressure, 45 g of perfluoroethyl iodide are recovered. 8 g of a solid brown product are isolated from the autoclave.

Sublimation yields 2.1 g of a beige telomer with a melting range of 130° to 150° C.

Mass spectroscopy and gas chromatography show:

$CF_3CF_2(CF_2CF_2)_nI$

| n | Molecular weight | Content, % |
|---|---|---|
| 4 | 646 | 11.49 |
| 5 | 746 | 14.69 |
| 6 | 846 | 4.90 |
| 7 | 946 | 0.80 |
| 8 | 1046 | 0.40 |
| $CF_3CF_2(CF_2CF_2)_nCH_2-CH_2-I$ | | |
| 3 *) | 574 | 14.69 |
| 4 *) | 674 | 24.49 |
| 5 *) | 774 | 19.59 |
| 6 *) | 874 | 6.52 |
| 7 *) | 974 | 1.63 |
| 8 *) | 1074 | 0.8 |

*) These by-products correspond to a compound of formula (2) on page 4.

The yield, relative to perfluoroethyl iodide consumed (at n = 5) is 12.73% of theory.

EXAMPLE 29

51 g of perfluorethyl iodide (0.207 mol), 55 g of tetrafluoroethylene (0.55 mol), 200 mg of zirconium tetrachloride and 5 g of morpholine are reacted according to the process of example 1.

The reaction starts at 120° C and 48 atmospheres gauge. The autoclave is kept at 120° C for 24 hours. In the course thereof, the pressure drops to 46 atmospheres gauge. On releasing the pressure, 40 g of perfluoroethyl iodide are recovered. 14 g of a semi-liquid product are isolated from the autoclave.

Sublimation yields 6.1 g of a white telomer with a melting point of 195° to 200° C.

Mass spectroscopy and gas chromatograpy show:

| A | | |
|---|---|---|
| \multicolumn{3}{c}{$CF_3CF_2(CF_2CF_2)_nI$ + $I(CF_2CF_2)_nI$} | | |
| n | Molecular weight | Content, % |
| 5 | 746 | 14.02 |
| 6 | 846 | 7.32 |
| 7 | 946 | 4.76 |
| 8 | 1046 | 6.38 |
| 9 | 1146 | 10.42 |
| 10 | 1246 | 10.28 |
| 4 | 654 | 2.93 |
| 5 | 754 | 2.37 |
| 6 | 854 | 2.86 |
| 7 | 954 | 1.64 |
| 8 | 1054 | 13.63 |
| 9 | 1154 | 10.31 |
| 10 | 1254 | 7.12 |
| 11 | 1354 | 5.96 |

(upper block labeled A, lower block labeled B)

The yield, relative to an average molecular weight of 1046, is 12.79% of theory.

As regards B: Perfluoroethylene diiodide has been produced by an exchange of fluorine for iodine between 2 molecules of perfluoroethyl iodide, and has also telomerised with tetrafluoroethylene.

EXAMPLE 30

52 g of perfluoroethyl iodide (0.211 mol), 4 g of tetrafluoroethylene (0.49 mol), 200 mg of zirconium tetrachloride and 5 g of N-hydroxyethylpiperazine are reacted according to the process of example 1.

The reaction starts at 140° C and 45 atmospheres gauge. The autoclave is kept at 140° C for 35 hours. In the course thereof, the pressure drops to 39 atmospheres gauge. On releasing the pressure, 42 g of perfluoroethyl iodide are recovered. 7 g of a brown solid product are isolated from the autoclave.

Sublimation yields 1 g of a yellow telomer with a melting range of 170° to 190° C.

Mass spectroscopy and gas chromatography show:

$CF_3CF_2(CF_2CF_2)_nI$

| n | Molecular weight | Content, % |
|---|---|---|
| 5 | 746 | 50.98 |
| 6 | 846 | 31.37 |
| 7 | 946 | 11.76 |
| 8 | 1046 | 3.92 |
| 9 | 1146 | 1.97 |

The yield, relative to an average molecular weight of 746, is 3.33% of theory.

EXAMPLE 31

51 g of perfluoroethyl iodide (0.207 mol), 50 g of tetrafluoroethylene (0.50 mol), 200 mg of zirconium tetrachloride and 5 g of diethylamine are reacted according to the process of example 1.

The reaction starts at 140° C and 45 atmospheres gauge. The autoclave is kept at 140° C for 38 hours. In the course thereof the pressure drops to 32 atmospheres gauge. On releasing the pressure, 45 g of perfluorethyl iodide are recovered. 13.7 g of a semi-solid product are isolated from the autoclave.

Sublimation yields 7.2 g of a white telomer with a melting point of 150° to 160° C.

Mass spectroscopy and gas chromatography show:

$CF_3CF_2(CF_2CF_2)_nI$

| n | Molecular weight | Content, % |
|---|---|---|
| 1 | 346 | 41.86 |
| 2 | 446 | 16.28 |
| 3 | 546 | 11.63 |
| 4 | 646 | 16.28 |
| 5 | 746 | 11.63 |
| 6 | 846 | 2.32 |

The yield, relative to an average molecular weight of 446, is 66.17% of theory.

EXAMPLE 32

50 g of perfluorethyl iodide (0.203 mol), 50 g of tetrafluorethylene (0.50 mol), 200 mg of zirconium tetrachloride and 5 g of glycine (= aminoacetic acid) are reacted according to the process of example 1.

The reaction starts at 120° C and 45 atmosphere gauge. The autoclave is kept for 38 hours at 120° C. In the course thereof, the pressure drops to 38 atmospheres gauge. On releasing the pressure, 45 g of perfluorethyl iodide are recovered. 16 g of a solid grey product are isolated from the autoclave.

Sublimation yields 9 g of a light yellow telomer with a melting point of 110° to 115° C. Mass spectroscopy and gas chromatography show:

$CF_3CF_2(CF_2CF_2)_nI$

| n | Molecular weight | Content, % |
|---|---|---|
| 3 | 546 | 9.69 |
| 4 | 646 | 17.82 |
| 5 | 746 | 15.22 |
| 6 | 846 | 29.65 |
| 7 | 946 | 19.28 |
| 8 | 1046 | 4.62 |
| 9 | 1146 | 1.24 |
| 10 | 1246 | 1.24 |
| 11 | 1346 | 1.24 |

The yield, relative to an average molecular weight of 746, is 59.40% of theory.

EXAMPLE 33

40 g of perfluorethyl iodide (0.163 mol), 50 g of tetrafluorethylene (0.50 mol), 200 mg of iron-II sulphate and 5 g of ethanolamine are reacted according to the process of example 1.

The reaction starts at 120° C and 45 atmospheres gauge. The autoclave is kept at 120° C for 48 hours. In the course thereof, the pressure drops to 40 atmospheres gauge. On releasing the pressure, 35 g of perfluorethyl iodide are recovered. 10 g of a solid brown product are isolated from the autoclave.

Sublimation yields 3.2 of a light yellow telomer with a melting point of 160 to 170° C.

Mass spectroscopy and gas chromatography show:

$CF_3CF_2(CF_2CF_2)_nI$

| n | Molecular weight | Content, % |
|---|---|---|
| 4 | 646 | 13.85 |
| 5 | 746 | 27.70 |
| 6 | 846 | 41.55 |
| 7 | 946 | 13.55 |
| 8 | 1046 | 2.77 |
| 9 | 1146 | 0.27 |

The yield, relative to an average molecular weight of 746, is 21.12% of theory.

EXAMPLE 34

20 g of perfluoro-n-propyl iodode (0.067 mol), 49 g of tetrafluorethylene (0.49 mol), 200 mg of yttrium trinitrate and 5 g of ethanolamine are reacted according to the process of example 1.

The reaction starts at 125° C and 26 atmospheres gauge. The autoclave is kept at 125° C for 35 hours. In the course thereof, the pressure drops to 25 atmospheres gauge. On releasing the pressure, 38 g of perfluoro-n-propyl iodidetetrafluorethylene mixtures are recovered. Content: 15.0 g of n-perfluoropropyl iodide. 6 g of a violet liquid, boiling point 77° to 88° C, are isolated from the autoclave.

Mass spectroscopy and gas chromatography show:

$CF_3CF_2CF_2(CF_2CF_2)_nI$

| n | Molecular weight | Content, % |
|---|---|---|
| 1 | 396 | 88.24 |
| 2 | 496 | 8.82 |
| 3 | 596 | 2.94 |

The yield, calculated relative to a molecular weight of 396, is 89.15% of theory.

EXAMPLE 35

48 g of perfluorisopropyl iodide (0.162 mol), 50 g of tetrafluorethylene (0.500 mol), 400 mg of tantalum pentaethylate and 5 g of ethanolamine are reacted according to the process of example 1.

The reaction starts at 142° C and 28 atmospheres gauge. The autoclave is kept at 140° C for 24 hours. In the course thereof, the pressure drops to 18 atmospheres gauge. On releasing the pressure, 20.3 g of perfluorisopropyl iodide are recovered. 14 g of a grey solid product are isolated from the autoclave.

Sublimation yields 8.86 g of a cream-coloured telomer with a melting point of 60° to 66° C.

Mass spectroscopy and gas chromatography show:

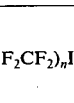

| n | Molecular weight | Content, % |
|---|---|---|
| 1 | 396 | 3.27 |
| 2 | 496 | 0.67 |
| 3 | 596 | 16.36 |
| 4 | 696 | 33.63 |
| 5 | 796 | 18.10 |
| 6 | 896 | 14.11 |
| 7 | 996 | 10.38 |
| 8 | 1096 | 3.05 |
| 9 | 1196 | 0.43 |

The yield, relative to an average molecular weight of 696, is 14.64% of theory.

EXAMPLE 36

49 g of perfluoromethyl iodide (0.250 mol), 40 g of tetrafluorethylene (0.40 mol), 200 mg of thallium-I carbonate and 5 g of ethanolamine are reacted according to the process of example 1.

The reaction starts at 140° C and 47 atmospheres gauge. The autoclave is kept at 140° C for 48 hours. In the course thereof, the pressure drops to 36 atmospheres gauge. On releasing the pressure, 44 g of perfluoromethyl iodide are recovered. 6.5 g of a brown viscous product are isolated from the autoclave.

Sublimation yields 3.55 g of a white telomer with a melting point of 88° to 95° C.

Mass spectroscopy and gas chromatography show:

$CF_3(CF_2CF_2)_nI$

| n | Molecular weight | Content, % |
|---|---|---|
| 3 | 596 | 31.60 |
| 4 | 696 | 22.75 |
| 5 | 796 | 14.35 |
| 6 | 896 | 10.20 |
| 7 | 996 | 15.80 |
| 8 | 1096 | 4.50 |
| 9 | 1196 | 0.80 |

The yield, relative to an average molecular weight of 696, is 20.28% of theory.

EXAMPLE 37

50 g of perfluoroheptyl iodide (0.101 mol), 52 g of tetrafluorethylene (0.52 mol), 200 mg of potassium cyanide and 5 g of ethanolamine are reacted according to the process of example 1.

The reaction starts at 140° C and 40 atmospheres gauge. The autoclave is kept at 140° C for 18 hours. In the course thereof, the pressure drops to 33 atmospheres gauge. On releasing the pressure, 58 g of perfluoralkyl iodide are recovered. 49 g of tetrafluorethylene are blown off.

Distillation yields 10.67 g of a liquid-solid telomer and 33.9 g of perfluoroheptyl iodide from 58 g of telomer.

Mass spectroscopy and gas chromatography show:

$CF_3(CF_2)_6(CF_2CF_2)_nI$

| n | Molecular weight | Content, % |
|---|---|---|
| 1 | 596 | 60.36 |
| 2 | 696 | 28.77 |
| 3 | 796 | 7.97 |
| 4 | 896 | 2.53 |
| 5 | 996 | 0.37 |

The yield, relative to a molecular weight of 596, is 62.84% of theory.

EXAMPLE 38

50 g of perfluorisopropyl iodide (0.169 mol), 49 g of tetrafluorethylene (0.49 mol), 200 mg of primary potassium orthophosphate ($KH_2PO_4$) and 5 g of ethanolamine are reacted according to the process of example 1.

The reaction starts at 140° C and 44 atmospheres gauge. The autoclave is kept at 140° C for 12 hours. In the course thereof, the pressure drops to 26 atmospheres gauge. On releasing the pressure, 37.9 g of perfluorisopropyl iodide are recovered. 23.7 g of a dark brown product are isolated from the autoclave.

Sublimation yields 18.6 g of a light yellow telomer with a melting point of 133° C.

Mass spectroscopy and gas chromatography show:

$$\begin{array}{c} CF_3 \\ \phantom{CF_3}\diagdown \\ \phantom{CF_3CF}CF(CF_2CF_2)_nI \\ \phantom{CF_3}\diagup \\ CF_3 \end{array}$$

| n | Molecular weight | Content, % |
|---|---|---|
| 3 | 596 | 31.95 |
| 4 | 696 | 40.24 |
| 5 | 796 | 20.12 |
| 6 | 896 | 7.10 |
| 7 | 996 | 0.59 |

The yield, relative to an average molecular weight of 696, is 65.26% of theory.

EXAMPLE 39

50 g of perfluorisopropyl iodide (0.169 mol), 47 g of tetrafluorethylene (0.47 mol), 200 mg of $ZrH_2$ and 5 g of ethanolamine are reacted according to the process of example 1.

The reaction starts at 140° C and 42 atmospheres gauge. The autoclave is kept at 140° C for 24 hours. In the course thereof, the pressure drops to 20 atmospheres gauge. On releasing the pressure, 22.2 g of perfluorisopropyl iodide are recovered. 47 g of a solid brown product are isolated from the autoclave.

Sublimation yields 25.4 g of a light yellow telomer with a melting point of 120 to 130° C.

Mass spectroscopy and gas chromatography show:

$$\begin{array}{c} CF_3 \\ \phantom{CF_3}\diagdown \\ \phantom{CF_3CF}CF(CF_2CF_2)_nI \\ \phantom{CF_3}\diagup \\ CF_3 \end{array}$$

| n | Molecular weight | Content, % |
|---|---|---|
| 1 | 396 | 1.85 |
| 2 | 496 | 0.93 |
| 3 | 596 | 2.86 |
| 4 | 696 | 41.59 |
| 5 | 796 | 37.89 |
| 6 | 896 | 10.17 |
| 7 | 996 | 2.77 |
| 8 | 1096 | 0.93 |
| 9 | 1196 | 0.92 |
| 10 | 1296 | 0.09 |

The yield, calculated relative to an average molecular weight of 796, is 33.98% of theory.

EXAMPLE 40

65 of trifluoromethylperfluorocyclohexane as the solvent, 20 g of perfluorisopropyl iodide (0.0676 mol), 40 g of tetrafluorethylene (0.40 mol), 200 mg of zirconium tetrachloride and 5 g of 3-diethylaminophenol are reacted according to the process of example 1.

The reaction starts at 95° C and 34 atmospheres gauge. The temperature immediately rises to 180° C (37 atmospheres gauge) and drops to 140° C (26 atmospheres gauge) over the course of 3 hours. The autoclave is kept at 140° C for 14 hours. In the course thereof, the pressure remains at 26 atmospheres gauge. On releasing the pressure, 16 g of perfluorisopropyl iodide are recovered. 75 g of a semi-solid product are isolated from the autoclave. 70 g of a mixture of trifluoromethylperfluorocyclohexane and 3-diethylaminophenol are distilled off. Sublimation yields 1.8 g of a cream-coloured telomer of melting point 125° to 137° C.

Mass spectroscopy and gas chromatography show:

$$\begin{array}{c} CF_3 \\ \phantom{CF_3}\diagdown \\ \phantom{CF_3CF}CF(CF_2CF_2)_nI \\ \phantom{CF_3}\diagup \\ CF_3 \end{array}$$

| n | Molecular weight | Content, % |
|---|---|---|
| 4 | 696 | 8.11 |
| 5 | 796 | 46.65 |
| 6 | 896 | 28.40 |
| 7 | 996 | 10.14 |
| 8 | 1096 | 4.06 |
| 9 | 1196 | 2.03 |
| 10 | 1296 | 0.61 |

The yield, calculated relative to an average molecular weight of 796, is 31.54% of theory.

I claim:

1. A process for the manufacture of fluoralkyliodides of higher molecular weight from the corresponding perfluoralkyliodides of lower molecular weight, which comprises telomerizing
   a. a perfluoralkyliodide selected from the group consisting of a branched perfluoralkyl mono- or di-iodide containing 1 to 10 carbon atoms and a linear perfluoralkyl mono- or di-iodide containing 1 to 10 carbon atoms,
   b. a member selected from the group consisting of tetrafluorethylene, hexafluorpropylene, trifluorethylene, trifluorochlorethylene and pentafluorchloropropylene, and
   c. a member selected from the group consisting of N-ethylethanalamine aminoethylisopropanolamine, diethylethanolamine, N-(2, hydroxyethyl)-ethylenediamine, isopropanolamine, tri-isopropanolamine, N-ethylethanalamine, N-methylethanolamine, diethanolamine, triethanolamine, monoethanolamine, N-hydroxy-ethylmorpholine, morpholine, N-hydroxyethylpiperazine, 3-diethylaminophenol, glycine and diethylamine, in the presence of
   d. a metal salt wherein said salt is a halide, phosphate, carbonate, nitrate, sulphate, cyanide, hydride or ethylate, of a metal of groups IIIa, IIIb to VIb and VIII of the 4th to 6th period or of groups Ia or IIa of the Periodic Table as the catalyst,
   at 0° to 350° C and under a pressure from 0 to 200 atmospheres (gauge).

2. A process according to claim 1, which comprises using as component a) a branched or linear perfluoralkyl mono- or di-iodide with 1 to 10 carbon atoms.

3. A process according to claim 1, which comprises using as component a) a branched or linear perfluoralkyl mono- or di-iodide with 1 to 3 carbon atoms.

4. A process according to claim 1, which comprises using as component b) tetrafluorethylene, hexafluorpropylene or trifluorchlorethylene.

5. A process according to claim 1, which comprises using as component (c) an amine which contains at least one hydroxyl group in the molecule.

6. A process according to claim 5, which comprises using as component (c) an alkanolamine.

7. A process according to claim 1, which comprises using as component (d) a metal salt of a metal of groups IIIb to VIIIb of the 4th to 6th period of the Periodic Table.

8. A process according to claim 1, which comprises using as component d) the metal salts of a metal of groups IIIb or VIIIb of the 4th or 5th period or the metal salt of a metal of groups IVb or Vb of the 4th to 6th period of the Periodic Table.

9. A process according to claim 1, which comprises using a component d) a metal halide selected from the group consisting of a chloride, a bromide and an iodide.

10. A process according to claim 1, which comprises telomerizing 1 mol of component (a) with 1 to 10 mols of component (b) and 0.05 to 10 mols of component (c) in the presence of 0.003 to 0.3 mol of component (d).

* * * * *